(12) United States Patent
Newkome et al.

(10) Patent No.: US 8,895,742 B2
(45) Date of Patent: Nov. 25, 2014

(54) METAL-MEDIATED REVERSIBLE SELF-ASSEMBLY OF CARBON NANOTUBES

(75) Inventors: George R. Newkome, Medina, OH (US); Charles N. Moorefield, Akron, OH (US); Pingshan Wang, Cuyahoga Falls, OH (US); Sinan Li, Akron, OH (US)

(73) Assignee: The University of Akron, Akron, OH (US)

( * ) Notice: Subject to any disclaimer, the term of this patent is extended or adjusted under 35 U.S.C. 154(b) by 1923 days.

(21) Appl. No.: 11/910,772

(22) PCT Filed: Apr. 7, 2006

(86) PCT No.: PCT/IB2006/051078
§ 371 (c)(1),
(2), (4) Date: Jul. 20, 2010

(87) PCT Pub. No.: WO2006/106491
PCT Pub. Date: Oct. 12, 2006

(65) Prior Publication Data
US 2010/0286395 A1 Nov. 11, 2010

Related U.S. Application Data

(60) Provisional application No. 60/669,124, filed on Apr. 7, 2005.

(51) Int. Cl.
| | | |
|---|---|---|
| *C07F 1/08* | (2006.01) | |
| *B82B 3/00* | (2006.01) | |
| *B82Y 40/00* | (2011.01) | |
| *B82Y 30/00* | (2011.01) | |
| *B82Y 10/00* | (2011.01) | |
| *B82Y 15/00* | (2011.01) | |

(52) U.S. Cl.
CPC . *B82B 3/00* (2013.01); *B82Y 40/00* (2013.01); *B82Y 30/00* (2013.01); *B82Y 10/00* (2013.01); *B82Y 15/00* (2013.01)
USPC .......................................................... 546/2

(58) Field of Classification Search
USPC .......................................................... 546/2
See application file for complete search history.

(56) References Cited

PUBLICATIONS

Banerjee, S. et al.: Functionalization of carbon nanotubes with a metal-containing molecular complex. Nano Letters, vol. 2, pp. 49-53, 2002.*
Banerjee, S. et al.: Structural characterization, optical properties, and improved solubility of carbon nanotubes functionalized with Wilkinson's catalyst. J. Am. Chem. Soc., vol. 124, pp. 8940-8948, 2002.*
Colasson, B.X., et al., "Irreversible but Noncovalent Ru(II)-Pyridine Bond: Its Use for the Formation of [2]-Catenanes," Inorg. Chem., 43, 1895-1901 (2004).
Sun, Y.P., et al., "Functionalized Carbon Nanotubes: Properties and Applications," Acc. Chem. Res., 35, 1096-1104 (2002).
Hirsch, A., "Functionalization of Single-Walled Carbon Nanotubes," Angew. Chem. Int. Ed., 41, 1853-1859 (2002).
Schmatloch, S., et al., "Metallo-Supramolecular Diethylene Glycol: Water-Soluble Reversible Polymers," Macromol. Rapid Commun., 23, 957-961 (2002).
Qin, S., et al., "Polymer Brushes on Single-Walled Carbon Nanotubes by Atom Transfer Radical Polymerization of n-Butyl Methacrylate," Am. Chem. Soc., 126, 170-176 (2004).
Ouyan, M., et al., "Fundamental Electronic Properties and Applications of Single-Walled Carbon Nanotubes," Acc. Chem. Res., 35, 1018-1025 (2002).
Holzinger, M., et al., "Sidewall Functionalization of Carbon Nanotubes," Angew. Chem. Int. Ed., 40, 4002-4005 (2001).
Bianco, A., et al., "Can Carbon Nanotubes Be Considered Useful Tools for Biological Applications?" Adv. Mater., 15, 1765-1768 (2003).
Lee, K.M., et al., "Asymmetric End-Functionalization of Multi-Walled Carbon Nanotubes," J. Am. Chem. Soc., 127, 4122-4123 (2005).
Fernando, K.A.S. et al., "Diminished Band-Gap Transitions of Single-Walled Carbon Nanotubes in Complexation with Aromatic Molecules," J. Am. Chem. Soc., 126, 10234-10235 (2004).
Mawhinney D.B. et al., "Surface Defect Site Density on Single Walled Carbon Nanotubes by Tritration," Chem. Phys. Lett. 347, 213-216 (2000).
Hamon, M.A. et al., "End-Group and Defect Analysis of Soluble Single-Walled carbon Nanotubes," Chem. Phys. Lett., 347, 8-12 (2001).
Zhao, B. et al., "Synthesis and Properties of a Water-Soluble Single-Walled Carbon Nanotube-Poly(m-aminobenzene sulfonic acid) Graft Copolymer," Adv. Funct. Mater., 14, 71-76 (2004).
Bottini, M. et al., "Covalent Decoration of Multi-Walled Carbon Nanotubes with Silica Nanoparticles," Chem. Commun, 758-760 (2005).
Sainsbury, T., "Carbon-Nanotube-Templated and Pseudorotaxane-Formation-Driven Gold Nanowire Self-Assembly,"-Chem. Mater., 16, 2174-2176 (2004).
Li, S., et al., "DNA-Directed Self-Assembling of Carbon Nanotubes," J. Am. Chem. Soc. 127, 14-15 (2005).
Basiuk, E.V., "Adsorption Modification of Single-Walled Carbon Nanotubes with Tetraazaannulene Macrocyclic Complexes," 2, 1249-1252 (2002).
Hemraj-Benny, T., et al., "Interactions of Lanthanide Complexes wtih Oxidized Single-Walled Carbon Nanotubes," Cham. Mater., 16, 1855-1863 (2004).
Banerjee, S., et al., "Rational Chemical Strategies for Carbon Nanotube Funcitonalization," Chem. Eur. J., 9, 1898-1908 (2003).

(Continued)

*Primary Examiner* — Charanjit Aulakh
(74) *Attorney, Agent, or Firm* — Renner Kenner Greive Bobak Taylor & Weber

(57) ABSTRACT

There is provided a method and nanocomposite for the reversible assembly of nanotubes, such as oxidized single wall carbon nanotubes, based on metal coordination. The method produces a thermally stable, neutral nanocomposite possessing enhanced mechanical, electrical, physical and chemical properties for example. Disassembly can be provided by treatment with a competing ligand compound.

6 Claims, 7 Drawing Sheets

(56) References Cited

PUBLICATIONS

Cao, L., "Fabrication of Rare-Earth Biphthalocyanine Encapsulated by Carbon Nanotubes Using a Capillary Filling Method," Chem. Mater., 15, 3247-3249 (2003).

Hofmeier, H. et al., "Recent Developments in the Supramolecular Chemistry of Terpyridine-Metal Complexes," Chem. Soc. Rev., 33, 373-399 (2004).

Wang, P. et al., "Helical and Polymeric Nanostructures Assembled From Benzene Tri- and Tetracarboxylic Acids Associated with Terpyridine Copper(II) Complexes," Chem. Commun., 465-467 (2005).

Erre, L.S. et al., "Molecular Structure and Spectral Properties of Bix(2,6-Dimethoxybenzoato)(2,2': 6',2"-terpyridine(II): A Five-Coordinate Mn(II) Complex," New J. Chem., 24, 725-728 (2000).

Seidel, S. R., et al., "High-Symmetry Coordination Cages via Self-Assembly," Acc. Chem. Res., 35, 972-983 (2002).

Fujita, M., et al., "Molecular Paneling via Coordination," Chem. Commun., 509-518 (2001).

Wang, P., et al., "Nanofabrication: Reversible Self-Assembly of an Imbedded Hexameric Metallomacrocycle within a Macromolecular Superstructure," Angew. Chem Int. Ed., 44, 1679-1683 (2005).

\* cited by examiner

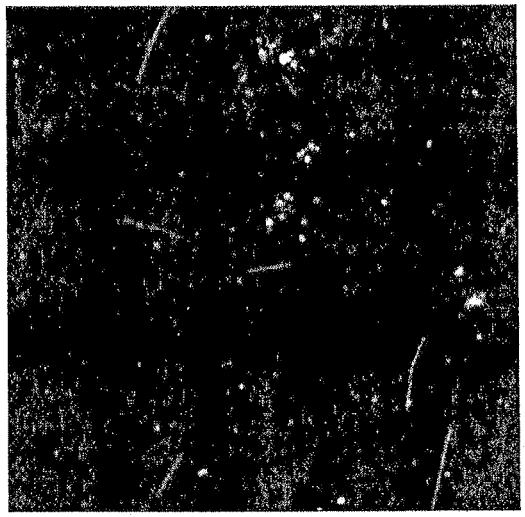
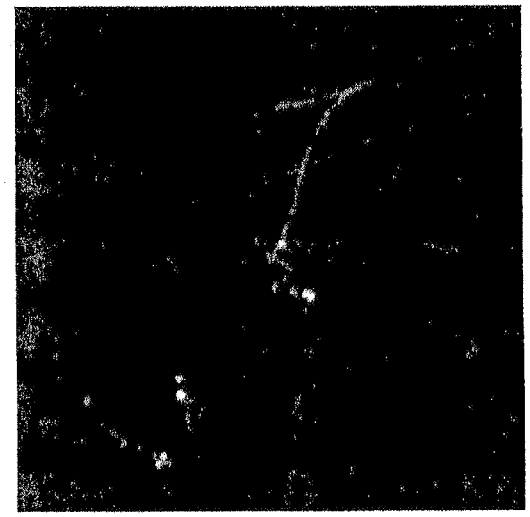
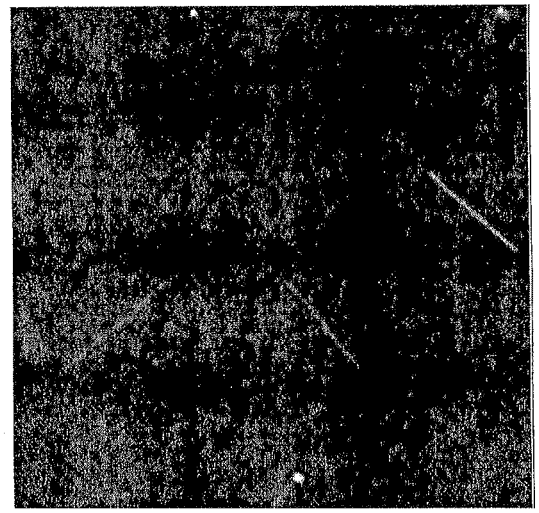
FIG. 5C
FIG. 5B
FIG. 5A

METAL-MEDIATED REVERSIBLE SELF-ASSEMBLY OF CARBON NANOTUBES

CROSS REFERENCE

This application claims priority to U.S. Provisional Application Ser. No. 60/669,124 filed on Apr. 7, 2005, which is incorporated herein by reference in its entirety.

GRANT REFERENCE

The research carried out in connection with this invention was supported in part by a grant from the National Science Foundation [DMR-0196231, DMR-0401780, CHE-0116041], the Air Force Office of Scientific Research (F49620-02-1-0428, 02), and the Ohio Board of Regents for financial support. The Government has certain rights in the invention.

TECHNICAL FIELD

The present invention relates to the reversible self-assembly of connected nanotubes. More specifically, the present invention relates to the preparation of connected nanotubes through the use of metal coordination chemistry.

BACKGROUND OF THE INVENTION

There have been developed a variety of nanomaterials, such as nanotubes, which may be beneficial for use in a variety of applications, such as electrical systems and networks. Carbon and other materials are formed into nanotubes, but there is a need to develop methodologies and systems to effectively utilize such materials. For example, modifications of single-wall carbon nanotubes (SWNT) can play an important role in exploring their chemical and physical properties, and using and enhancing such properties for different applications. To date, SWNTs have been successfully functionalized with covalent and non-covalent surface modifications employing 1,3-dipolar cycloadditions, photoinduced addition, $\pi$-$\pi$ interaction, to mention but a few. Also, metallopolycarboxylate coordination has been commonly used for the construction of zeolitic, cage, and paddle-wheel architectures via the use of transition, main-group, and rare earth metals as well as a number of hybrid metal structures. Oxidized single-wall carbon nanotubes (Oxi-SWNT), possessing carboxylic acids on the open-ends and sidewall, have been modified by introducing various organic functional groups, including DNA. Also, new strategies for introducing immobilized metals and their complexes onto, as well as into, carbon nanotubes have been reported.

As a result of the thermal stability, robust chemical properties, and electron and energy transfer characteristics, metal-based complexes of bis(2,2':6'2''-terpyridine) (tpy-M-tpy, where tpy=terpyridine and M=metal) have been widely investigated in a host of applications. Recently, it was reported that the assembly of terpyridine-copper-carboxylate complexes possessing a pentacoordinate geometry, in which this $Cu^{II}$ complexation involves three metal-N bonds and two cis-oriented sites (carboxylate ions). The available cis-oriented sites allow for the substitution of the aryl polycarboxylic acids with various agents; in this case, Oxi-SWNTs were introduced. These terpyridine-metal-carboxylate complexes are vulnerable to degradation under basic conditions or in the presence of competitive reagents. It has also been shown that the combination of SWNTs with photoactive electron donors, such as porphyrins or bipyridine ruthenium complexes, has been developed for potential applications in solar energy conversion utilizing the electron-acceptor character of the SWNTs.

It would be advantageous to provide a method of self-assembly of single-wall carbon nanotubes wherein the self-assembly process occurs by at least one metal mediated moiety, to provide the ability to create self-assembled nanostructures and also enhance the functionality or characteristics of the nanotube materials. It would also be advantageous to provide a method of self-assembly of nanotubes wherein the methodology can be used to create different structural morphologies, and can undergo quantitative disassembly by treatment with a competing ligand compound.

SUMMARY OF THE INVENTION

It is, therefore, an aspect of the present invention to provide a method of preparing the self-assembly of connected nanotubes to produce a composite material having enhanced properties and/or characteristics, through the use of metal coordination chemistry. The method may also provide for the assembly of nanotubes to be reversible.

It is another aspect of the present invention to provide a method of preparing a nanocomposite, the method includes the steps of reacting a plurality of nanotubes with a metal complex in a solvent system to form an assembled complex. The assembled complex may be disassembled upon treatment with a competing ligand compound.

A further aspect of the present invention is to provide a metallo-nanomaterial that includes a plurality of nanotubes coordinated with a metal complexing agent. The nanotubes may be carbon nanotubes for example, and the metal complexing agent may be a metal pyridine compound for example, where the metal portion of the compound is copper (II) and the ligating portion is selected from the group consisting of functionalized monopyridines, bispyridines, and polypyridine ligands. Other monotopic, ditopic and polytopic (i.e., monocoordinating and polycoordinating) ligands may be suitable, such as diphos and di- or tri-amino alkanesor the like. The ligands may be modified by known procedures with substituents the can affect network and nanotube mechanical, electrical, physical and chemical properties. This can be extended to the construction of dendritic arrays, quantum dots and directed and self-assembled multi-metal arrays. Attached substituents can be connected to the nanotube and/or ligating specie and can include fractal-based molecules and polymers that allow for the construction of precisely designed and architecturally controlled nanoscale molecular species.

Applications for these composite materials include their use in sensors and detectors, catalysis, photovoltaic components and devices in combination with photoactive electron donors, light-emitting diodes, semiconductors, bio-sensors, nanoscale electronic components, nanoreactors, energy collection and storage, mechanical and electronic materials modifiers for incorporation in such materials as cloth, other composite materials, ceramics, polymers, plastics, rubbers, maleable and ductile materials, and glass.

The metallo-nanomaterial may have a configuration selected from the group consisting of head-to-head, head-to-wall and wall-to-wall. The metallo-nanomaterial may be disassembled upon treatment with a competing ligand. This can prove useful to effect a desired physicochemical property, such as the emission of energy, followed by the halting of the phenomena via disassembly of the network. Control of oxidation sites on the nanotube facilitates control of nanotube attachment architecture and thus control of network architecture. For example, nanotubes oxidized only on the ends when treated with a 1 to 2 branched trisligand can result in dendritic nanotube arrays that are capable of collecting energy and funneling it to a localized site. This can work in an opposite manner to disperse energy over a desired area.

It is another aspect of the present invention to provide a plurality of oxidized single-wall carbon nanotubes coordinated with a first metal complex having a first metal portion and a second metal complex having a second metal portion to form an assembled complex, where the first metal portion of the first complex is different than the second metal portion of the second complex. A logical extension of the use of multiple metals is their use in a combinatorial-type manner where mixing metals results in the ability to tune and adjust electrical or absorption/emission properties.

Another aspect of the present invention includes a method of reversibly assembling nanocomposites that includes the steps of reacting a plurality of oxidized carbon nanotubes with a metal complex in a solvent system to form an assembled complex and disassembling the assembled complex upon treatment with a competing ligand compound. This process is repeatable as desired.

This and other advantages of the present invention are achieved by the method as described in more detail below.

The present invention relates to the reversible self-assembly of connected nanotubes. More specifically, the present invention relates to the preparation of connected nanotubes through the use of metal coordination chemistry.

Figure 1:
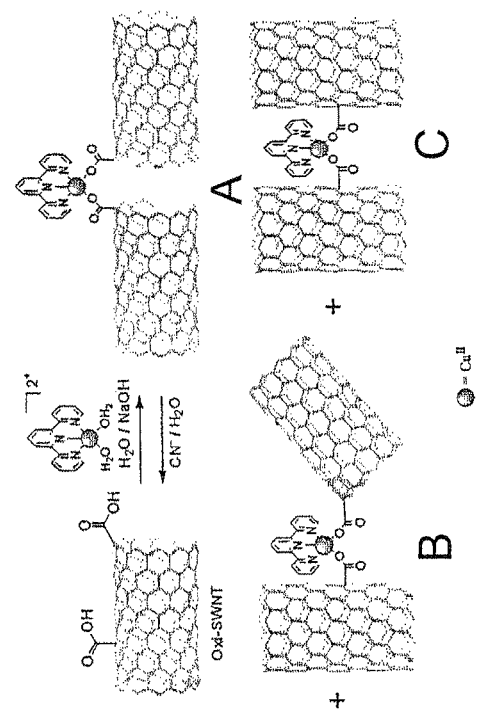
FIG. 1 is a schematic representation of the assembly and disassembly of the compounds of the present invention; (1A) head-to-head, (1B) head-to-wall, and (1C) wall-to-wall coordination.
Figure 2A:
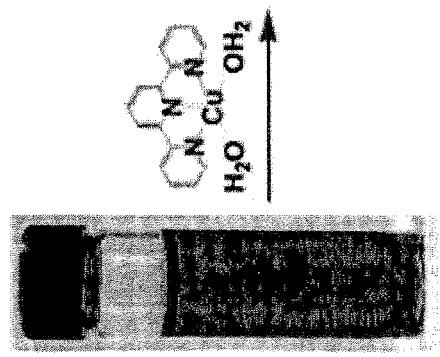
FIG. 2A is a representative photograph showing a solution of oxidized single-wall carbon nanotubes.
Figure 2B:
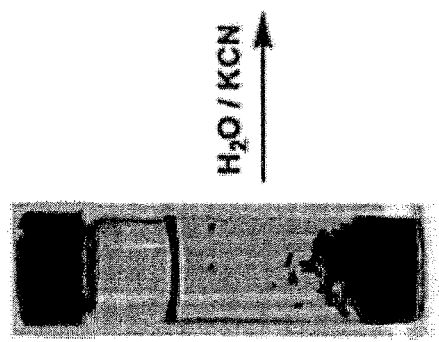
FIG. 2B is a representative photograph showing the reaction product of oxidized single-wall carbon nanotubes with a metal based complex.
Figure 2C:
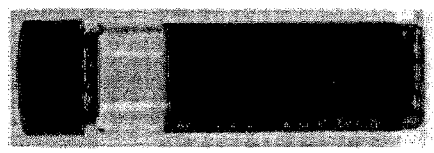
Figure 2E:
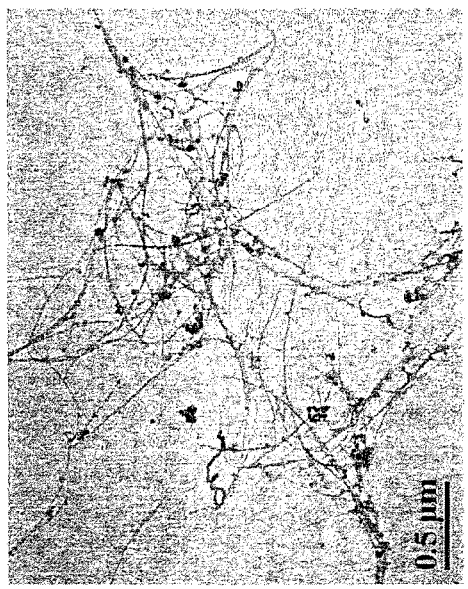
Figure 2D:
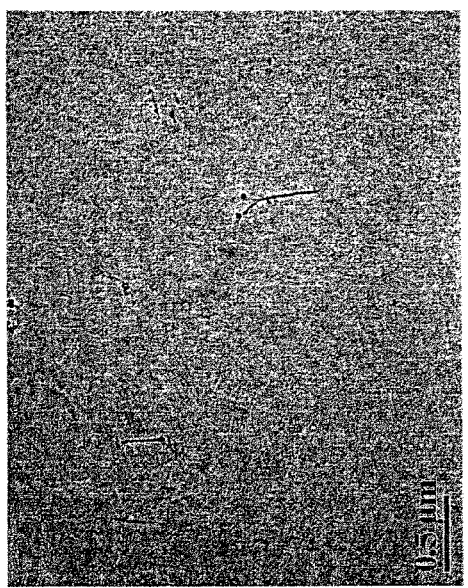
Figure 2F:
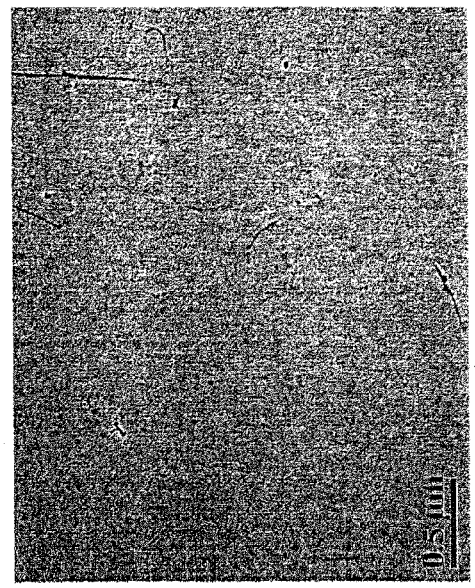
Figure 3B:
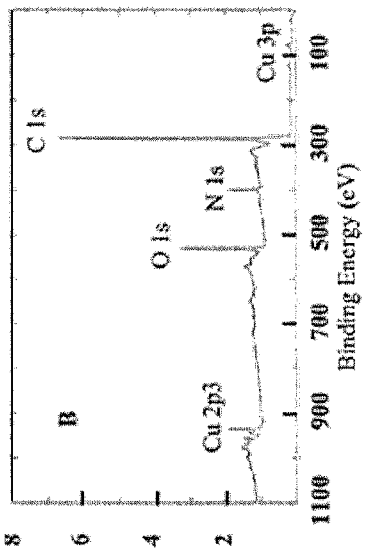
Figure 3A:
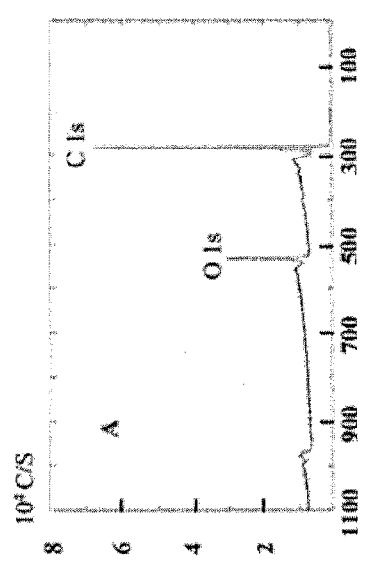
Figure 4B:
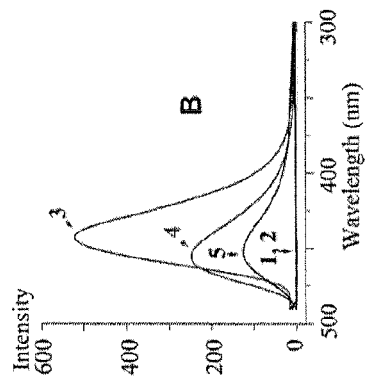
Figure 4A:
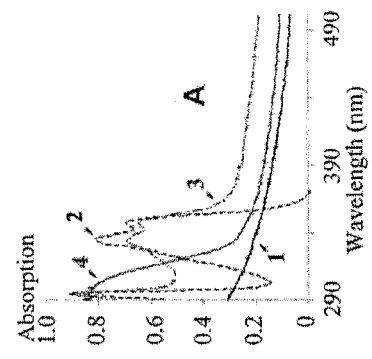
Figure 6C:
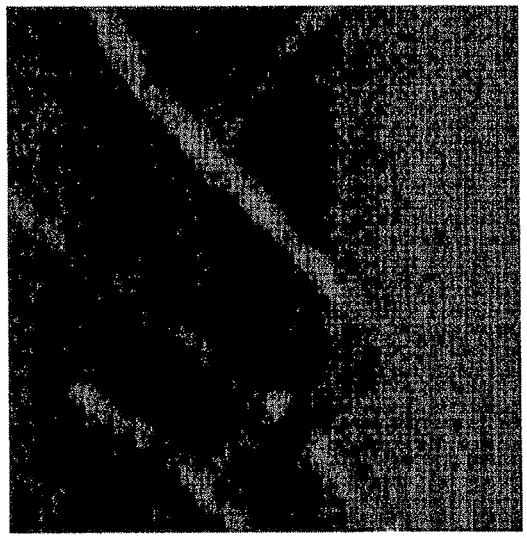
Figure 6B:
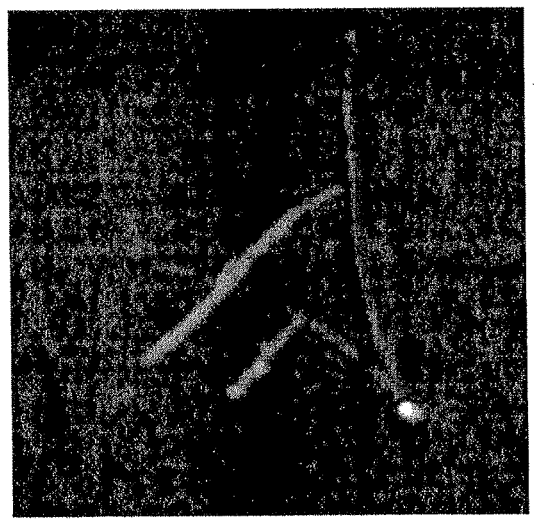
Figure 6A:
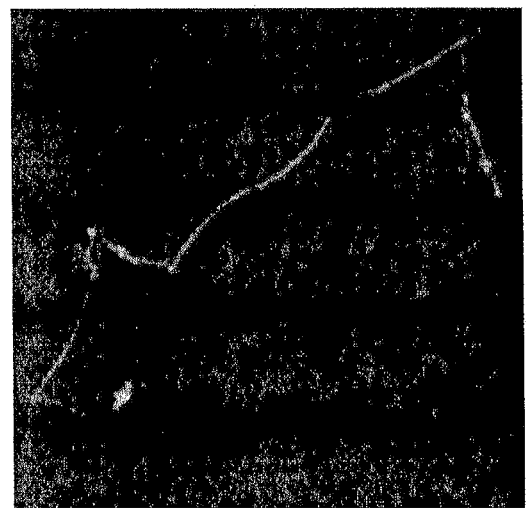
Figure 7:
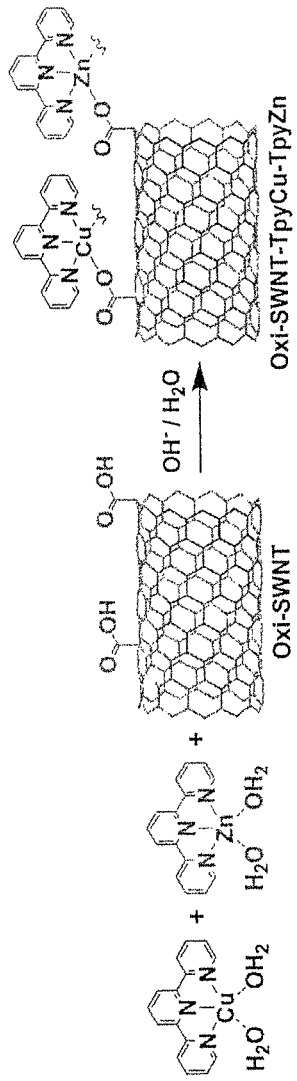
Figure 8:
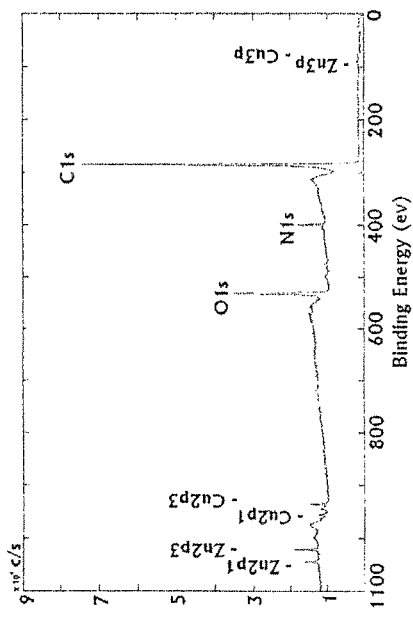

FIG. 2C is a representative photograph showing the disassembly of the reaction product as prepared in FIG. 2B with a competing ligand compound;

FIG. 2D is a transmission electron microscope image of the unreacted oxidized single-wall carbon nanotubes in solution;

FIG. 2E is a transmission electron microscope image of the reaction product formed in FIG. 2B;

FIG. 2F is a transmission electron microscope image of the disassembled reaction product as prepared in FIG. 2C;

FIG. 3A is a XPS spectra of a neat oxidized single-wall carbon nanotubes;

FIG. 3B is a XPS spectra of oxidized single-wall carbon nanotube complex;

FIG. 4A is a UV-VIS absorption spectra of the assembly and disassembly of the tpyCu$^{II}$ starting reagent and oxidized single-wall carbon nanotubes;

FIG. 4B is the emission spectra of the assembly and disassembly of the tpyCu$^{II}$ starting reagent and oxidized single-wall carbon nanotubes;

FIG. 5A is an atomic force microscopy image showing oxidized single-wall carbon nanotubes;

FIG. 5B is an atomic force microscopy image showing hyperbranched oxidized single-wall carbon nanotubes by coordination;

FIG. 5C is an atomic force microscopy image showing disassociated oxidized single-wall carbon nanotubes;

FIG. 6A is an atomic force microscopy image showing oligomeric, head-to-head oxidized single-wall carbon nanotubes;

FIG. 6B is an atomic force microscopy image showing oligomeric, head-to-wall oxidized single-wall carbon nanotubes;

FIG. 6C is an atomic force microscopy image showing oligomeric wall-to-wall oxidized single-wall carbon nanotubes;

FIG. 7 is a schematic representation illustrating the assembly of oxidized single wall carbon nanotubes complexed with mixed terpyridineCu$^{II}$ and terpydineZn$^{II}$; and FIG. 8 is XPS spectra of Oxi-SWNT-tpyCu$^{II}$-tpyZn$^{II}$ film.

DETAILED DESCRIPTION OF THE INVENTION

The present invention will be described in relation to specific embodiments, with reference to the drawings. In a first embodiment, as will be described in relation to FIGS. 1-6, the reversible self-assembly of connected nanotubes, more specifically, this embodiment relates to the self-assembly of Oxi-SWNTs mediated by tpyCu$^{II}$ resulting in angular- and cross-linked nanotube network connectivity and its quantitative disassembly upon treatment with excess potassium cyanide. This method results in the preparation of nanocomposites of carboxylate-modified SWNTs mediated by tpyCu$^{II}$ resulting in nanotube assembly and, while structurally stable, its facile disassembly in the presences of competing ligands.

Oxi-SWNT (10 mg) (purchased from Aldrich: carboxylic acid; 3-6 atom %; 4-5 nm×500-1500 nm) in aqueous NaOH (1.5 mg) was treated with tpyCu (3 mg), which was prepared by reaction of terpyridine with Cu(BF$_4$)$_2$ under aqueous conditions. A black precipitate immediately formed and the aqueous solution became completely colorless indicative of quantitative formation of [tpyCu-(Oxi-SWNT)$_m$]$_n$ complexes (A→B; FIGS. 2A and 2B). Washing the product with copious amounts of water through a nylon filter (0.2 μm, Millipore Corp.) gave the mixture of assembled complexes. The Oxi-SWNT/tpyCu complexes were observed to possess good thermal stability, as shown by no structural change in water at 100° C. for 12 hours, which was evidenced by TEM images. Their disassembly was readily induced by suspension of the complexes (2 mg) in water at 25° C. with KCN (1 mg) for 4 hours resulting in a translucent pale green solution as shown in (B→C; FIGS. 2B and 2C).

Since the carboxylic acids on the Oxi-SWNT are located on both of the open-ends as well as sidewalls, the self-assembly with tpyCu gives rise to three different configurations: head-to-head (FIG. 1A), head-to-wall (FIG. 1B), and wall-to-wall (FIG. 1C).

Morphological observations were conducted by transmission electron (TEM) and atomic force (AFM) microscopies. For the TEM a dilute sample (100 μg/100 ml) was cast onto a carbon-covered grid (Cu or Ni, 400 mesh, SPI Corp.). TEM analysis (FIG. 2D) visibly proved the morphologies of the Oxi-SWNT in association with tpyCu$^{II}$. Since the carboxylic acids on Oxi-SWNT are located on both the open-ends as well as the sidewalls, our observations indicated that the functional carboxylic moieties on the SNWT's open-ends are more likely to complex with tpyCu$^{II}$ than those on the side wall due to enhanced site availability. When comparing the TEM of the nanocomposite (FIG. 2E) with that of the TEM of starting Oxi-SWNT (FIG. 2D) and resulting disassociated complex (FIG. 2F), different patterns for the complex [(Oxi-SWNT)(tpyCu$^{II}$)$_m$]$_n$ could easily be distinguished from the presence of large particles that are a result of the typical residual metal catalyst contamination found in the commercial samples. The nanotubes of neat Oxi-SWNT were well distributed over the grids; whereas, the complexed [(Oxi-SWNT)(tpyCu$^{II}$)$_m$]$_n$ generally formed networks. After subjection to KCN, the [tpyCu-(Oxi-SWNT$_m$]$_n$ complex was completely destroyed, and TEM images revealed individual nanotubes (FIG. 2E) which were consistent with precomplexed Oxi-SWNT images in size and length.

X-ray photoelectron spectroscopic (XPS, monochromatic Mg Kα radiation at a power of 250 W, 93.90 eV) measurements for the parent Oxi-SWNT (FIG. 3A) showed typical graphite-carbon-like peaks (C1s) at 285 eV and O1s (from oxidized carbon) at 531 eV. The complexed [(Oxi-SWNT)(tpyCu$^{II}$)$_m$]$_n$ (FIG. 3B) showed new peaks attributed to N1s at 398 eV along with other new peaks assigned to Cu (2p$^{1/2}$ at 953 eV and 2p$^{3/2}$ at 933 eV) thereby confirming the nanocomposite. The atomic O/C ratio (17.6), as determined by XPS, of neat Oxi-SWNT was reduced to 16.4 after complexing with tpyCu$^{II}$ affording further evidence for the association. The reaction of SWNT-COONa and tpyCu$^{II}$(BF$_4$)$_2$ produced [(Oxi-SWNT)(tpyCu$^{II}$)$_m$]$_n$ and the by-product, NaBF$_4$. Each of these products was easily removed by multiple washings with water. The XPS of the composite showed no evidence of either Na$^+$ or BF$_4^-$ (Na1s is at 1072 eV and F1s at 685 eV).

In FIG. 4A, a comparison of the UV-vis absorption data or spectra for the starting reagents (tpyCu$^{II}$), labeled as line (2) in FIG. 4A, and [Oxi-SWNT], labeled as line (1) in FIG. 4A, and the composite [(Oxi-SWNT)(tpyCu$^{II}$)$_m$]$_n$, labeled as line (3) in FIG. 4A, revealed a slight bathochromic shift (ca. 1-2 nm) for the metal-ligand absorbance between tpyCu$^{II}$ and [(Oxi-SWNT)(tpyCu$^{II}$)$_m$]$_n$; the intensity was, however, suppressed after functionalization. Disassembly of the complex, labeled as line (4) in FIG. 4A, revealed the disappearance of metal complex peaks at 320-340 nm supporting the absence of terpyridine-based connectivity, which is consistent with the TEM and AFM observations. The photoluminescence experiments were conducted in aqueous suspension or solution at the same concentrations (~2×10$^{-7}$ M) with an excitation wavelength of 290 nm. The corresponding emission spectra are shown in FIG. 4B. The starting reagents of [Oxi-SWNT] and (tpyCu$^{II}$) are labeled as lines (1) and (2) respectively in FIG. 4B. The clear photoluminescence for [(Oxi-SWNT)(tpyCu$^{II}$)$_m$]$_n$, labeled as line (3) in FIG. 4B, was observed with a strong emission peak at =357 nm. After disassembly, as seen in line (4) of the [Oxi-SWNT)(tpyCu$^{II}$) and line (5) of the tpyCu$^{II}$ complex, a new peak at 347 nm appeared which was also observed after treatment of the starting tpyCu$^{II}$ with aqueous cyanide suggesting that this peak is due to Cu—CN coordination.

To further confirm the coordination-directed complexation and disassembly process, a droplet of the resultant suspension (100 μg/500 ml in DI water) was deposited on the surface of freshly cleaved mica and dried under ambient conditions. FIGS. 5A-5C show the AFM images for the pure Oxi-SWNT. It is noted that in FIG. 5A, the bright particles are for the contaminated metal catalyst in these commercial complex and disassociated Oxi-SWNTs as shown in FIG. 5C, in which the isolated nanotubes where tubular lengths (<2 μm) and diameter (4±1.5 nm) are clearly shown. FIG. 5B shows the [(Oxi-SWNT)(tpyCu$^{II}$)$_m$]$_n$ composite. Prior studies have shown that less than 2% connections for the pristine nanotubes, compared to 30% intermolecular nanotube junctions derived from amide cross-linking. Analysis of the AFM and TEM images gives rise to a possible inter-connectivity network for the [(Oxi-SWNT) (tpyCu$^{II}$)$_m$]$_n$ suggesting a more than 80% cross-linked assembly.

Numerous differing linkages, as shown in FIGS. 6A-6C, were observed that further confirm the formation of inter-nanotube junctions mediated by the two reaction sites of tpyCu$^{II}$Self-assembly of the SWNTs with tpyCu$^{II}$ connectivity gives rise to the possible linkages, such as head-to-head (V model), head-to-wall (T or Y models), and a few wall-to-wall (X model) due to the more hindered wall-sites of the Oxi-SWNTs of which the first two modes of connectivity are favored; these assembly combinations were formed in a ratio of 5:6:1, respectively. These structures include nanotubes connected in oligomeric, multinanotube head-to-head nanotubes connected in oligomeric, multinanotube head-to-head motif, as shown in FIG. 6A, a head-to-wall motif, as shown in FIG. 6B, and wall-to-wall motif, as shown in FIG. 6C. The branching observed in these assemblies is attributed to the formation of coordination linkages between the open end-modified and sidewall-modified Oxi-SWNTs through a common tpyCu$^{II}$ complex. Therefore, these results suggest that random connection of the carbon nanotubes with coordination complexes are capable of leading to the formation of hyperbranched nanotube assemblies, wherein the coordination of only end-oxidized nanotubes with mono- or polypyridine ligands should afford linear and dendritic arrays, respectively. It should also be possible to control coordination and connection between nanotubes to precisely control the architecture of the formed nanocomposite. The ligands may also be modified by known procedures with substituents the can affect network and nanotube mechanical, electrical, physical and chemical properties. This can be extended to the construction of dendritic arrays, quantum dots and directed and self-assembled multi-metal arrays. Attached substituents can be connected to the nanotube and/or ligating specie and can include fractal-based molecules and polymers that allow for the construction of precisely designed and architecturally controlled nanoscale molecular species.

The metallo-nanomaterial may also enable other connections besides the head-to-head, head-to-wall and wall-to-wall configurations to provide flexibility in creating a desired architecture. The metallo-nanomaterial may be disassembled upon treatment with a competing ligand. This can prove useful to affect a desired physicochemical property for example, such as the emission of energy, followed by the halting of the phenomena via disassembly of the network. Control of oxidation sites on the nanotube facilitates control of nanotube attachment architecture and thus control of network architecture. For example, nanotubes oxidized only on the ends when treated with a 1 to 2 branched trisligand can result in dendritic nanotube arrays that are capable of collecting energy an funneling it to a localized site. This can work in an opposite manner to disperse energy over a desired area. In an embodiment of the present invention, the self-assembly of the Oxi-SWNT with tpyCu can be directed to form a specific configuration, either head-to-head or wall-to-wall. This coordinated self-assembly can be accomplished by using Oxi-SWNTs having a known location for the carboxylic acid functionality. In this way, if the carboxylic acid functionality is located only at the open-ends or the sidewalls of the Oxi-SWNT, then a nanocomposite having only a head-to-head or a wall-to-wall configuration can be constructed. Thus, these nanocomposite materials having a single specific, uniform configuration can be used in a desired end-use application, such as circuit boards, transistors and other electronic devices.

In a further embodiment of the present invention, mixed metal-SWNT composites have been prepared. These mixed metal-SWNT focused on the use of the terpyridine Cu$^{II}$ and Zn$^{II}$ adducts as seen in FIG. 7. A terpyridineZn$^{II}$ complex was prepared in the same manner as that of the terpyridineCu adduct using $Zn(BF_4)_2$. A mixed aqueous solution of tpyCu$^{II}$ (1 mg/ml) and tpyZn$^{II}$ (1 mg/ml) was added to a basic Oxi-SWNT aqueous solution (10 mg in 20 ml of water containing 1.0 mg of sodium hydroxide). The immediately formed precipitate was sonicated at 50° C. for 2 hours; the black solid (11.2 mg) was collected by filtration through a nylon filter (0.2 μm), and finally washed with large amounts of water and acetonitrile (2×5 ml). Evidence of no residual or unreacted terpyridine metal complex was confirmed by monitoring the clear aqueous reaction solution by TLC (SiO2, eluent; MeCN:saturated aqueous $KNO_3$:water, 10:1:1).

Formation of the mixed metal [(Oxi-SWNT)(tpyCu$^{II}$)$_m$ (tpyZn$^{II}$)$_{m'}$]$_n$ composite was further confirmed via χ-ray photoelectron spectroscopy (XPS) as seen in FIG. 9. Compared to the pristine Oxi-SWNTs spectrum (FIG. 3A), the mixed metal hybrids spectrum, as seen in FIG. 8, exhibited new peaks attributed to nitrogen (N1s at 398 eV), Cu (2p$^{1/2}$ at 953 eV and 2p$^{3/2}$ at 933 eV) and Zn (2p$^{1/2}$ at 1045 eV and 2p$^{3/2}$ at 1022 eV), no peaks corresponding to Na$^+$ and $BF_4^-$ was observed. The atomic O/C ratio (17.6%) of unassembled Oxi-SWNT decreased to 16.9% after complexation providing further evidence of attachment of Cu$^{II}$ and Zn$^{II}$ adducts.

Therefore, it has been shown that the self-assembly of Oxi-SWNTs, based on terpyridineCu$^{II}$ coordination, produced a thermally stable, neutral [(Oxi-SWNT)(tpyCu$^{II}$)$_m$]$_n$ composite and disassembly of the composite occurred upon treatment with aqueous KCN. Similarly, it has been show that it is possible to produce a mixed metal [(Oxi-SWNT)(tpy-Cu$^{II}$)$_m$(tpyZn$^{II}$)$_{m'}$]$_n$ composites. The invention provides new and simple methods to assemble and disassemble electrically conductive organic nanotubes, in a nearly quantitative procedure. The controlled, self-assembly for the construction of nanotube lattices with metal complexes gives rise to a new strategy for building metallo-nanomaterials that could find potential application in nanoscale electronic devices. The ligands may be modified by known procedures with substituents the can affect network and nanotube mechanical, electrical, physical and chemical properties. This can be extended to the construction of dendritic arrays, quantum dots and directed and self-assembled multi-metal arrays. For example, the nanotubes may be modified with quantum dots, such as CdS. Attached substituents can be connected to the nanotube and/or ligating specie and can include fractal-based molecules and polymers that allow for the construction of precisely designed and architecturally controlled nanoscale molecular species having desired mechanical, electrical, physical and/or chemical characteristics or properties that may be tailored for a specific application. The nanocomposite materials of the invention may be used in various applications, including but not limited to their use in sensors and detectors, catalysis, photovoltaic components and devices in combination with photoactive electron donors, light-emitting diodes, semiconductors, bio-sensors, nanoscale electronic components, nanoreactors, energy collection and storage, mechanical and electronic materials modifiers for incorporation in such materials as cloth, other composite materials, ceramics, polymers, plastics, rubbers, malleable and ductile materials, and glass.

It is an aspect of the present invention to provide the ability to form multi-metal arrays, wherein a plurality of nanotubes may be coordinated with a first metal complex having a first metal portion, as well as by a second metal complex having a second metal portion. This provides the ability to form an assembled complex, where the first metal portion of the first complex is different than the second metal portion of the second complex. A logical extension of the use of multiple metals is their use in a combinatorial-type manner where mixing metals results in the ability to tune and adjust electrical or absorption/emission properties, or other characteristics of the nanocomposite.

To illustrate the invention, it is shown and described with respect to specific embodiments. This is not intended as a limitation, and other modifications or variations in the specific form shown and described will be apparent to those skilled in the art. The embodiments were chosen and described in order to best explain the principles of the invention and practical applications to thereby enable a person skilled in the art to best utilize the invention and various embodiments with various modifications as are suited to the particular use contemplated.

What is claimed is:

1. A metallo-nanomaterial comprising: first and second carbon nanotubes, each nanotube having a ligating component; and a metal complex selected from copper terpyridine metal complexes and zinc terpyridine metal complexes, wherein the ligating component of each of the first and second carbon nanotubes coordinates with the metal complex such that the metal complex connects the first and second carbon nanotubes.

2. The metallo-nanomaterial of claim 1 where the carbon nanotubes are selected from the group consisting of organic nanotubes, inorganic nanotubes, single-wall nanotubes and multi-wall nanotubes.

3. The metallo-nanomaterial of claim 2 where the carbon nanotubes are oxidized carbon nanotubes having carboxylic acid functionality.

4. The metallo-nanomaterial of claim 1 where the ligating component is selected from the group consisting of functionalized or unfunctionalized mono- and polytopic species.

5. The metallo-nanomaterial of claim 1 where the nanotubes of the metallo-nanomaterial are connected having a configuration selected from the group consisting of head-to-head, head-to-wall and wall-to-wall connections.

6. The metallo-nanomaterial of claim 4 where the metallo-nanomaterial is disassembled upon treatment with a competing ligand.

* * * * *